United States Patent [19]

Klages et al.

[11] Patent Number: 5,071,752
[45] Date of Patent: Dec. 10, 1991

[54] PROCESS FOR THE PRODUCTION OF L-AMINO ACIDS

[75] Inventors: Uwe Klages; Alfred Weber, both of Berlin; Ludwig Wilschowitz, Neusaess, all of Fed. Rep. of Germany

[73] Assignee: Schering Aktiengesellschaft, Berlin and Bergkamen, Fed. Rep. of Germany

[21] Appl. No.: 272,836

[22] PCT Filed: Jan. 22, 1988

[86] PCT No.: PCT/DE88/00037

§ 371 Date: Sep. 23, 1988

§ 102(e) Date: Sep. 23, 1988

[87] PCT Pub. No.: WO88/05468

PCT Pub. Date: Jul. 28, 1988

[30] Foreign Application Priority Data

Jan. 23, 1987 [DE] Fed. Rep. of Germany ....... 3702384

[51] Int. Cl.$^5$ ............ C12P 41/00; C12P 13/12; C12P 13/06; C12P 13/04
[52] U.S. Cl. ............... 435/113; 435/106; 435/107; 435/108; 435/110; 435/114; 435/115; 435/116; 435/253.2; 435/280; 435/872; 435/109
[58] Field of Search ............ 435/280, 872, 253.2, 435/116, 115, 113, 109, 114, 106, 107, 108, 110

[56] References Cited

U.S. PATENT DOCUMENTS

| | | | |
|---|---|---|---|
| 4,094,741 | 6/1978 | Yamada et al. | 435/280 X |
| 4,211,840 | 7/1980 | Nakamori et al. | 435/116 X |
| 4,237,227 | 12/1980 | Yamada et al. | 435/280 X |
| 4,242,452 | 12/1980 | Yamada et al. | 435/280 X |

FOREIGN PATENT DOCUMENTS

| | | | |
|---|---|---|---|
| 177991 | 8/1986 | Japan | 435/106 |
| 181391 | 8/1986 | Japan | 435/106 |
| 285995 | 12/1986 | Japan | 425/106 |
| 111692 | 5/1987 | Japan | 435/106 |
| 112990 | 5/1988 | Japan | 435/106 |
| 2042531 | 9/1980 | United Kingdom . | |

OTHER PUBLICATIONS

CA 93:43950x (1980).
CA 707:5729g (1987).

Primary Examiner—Carolyn Elmore
Attorney, Agent, or Firm—Millen, White & Zelano

[57] ABSTRACT

Process is described for the production of L-amino acids of general formula I

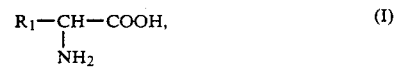

in which $R_1$ means an alkyl radical with at most 12 carbon atoms optionally substituted by hydroxy groups, mercapto groups, halogen atoms, amino groups, carbonyl groups or guanidino groups and/or interrupted by oxygen atoms, nitrogen atoms or sulfur atoms, and in the case of mercapto compounds of formula I also their dithio compounds, characterized in that the microorganism Nocardia spec. DSM 3306 or its enzymes are allowed to act on a D,L-imidazolidinedione derivative of general formula II

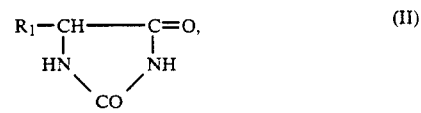

in which $R_1$ has the above-named meaning or, in the case of mercapto compounds of formula II, also in their dithio compounds.

8 Claims, No Drawings

PROCESS FOR THE PRODUCTION OF L-AMINO ACIDS

The invention relates to a process for the production of L-amino acids of general formula I

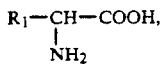

$$R_1-CH-COOH, \quad (I)$$
$$\phantom{R_1-CH-}NH_2$$

in which $R_1$ means an alkyl radical with at most 12 carbon atoms optionally substituted by hydroxy groups, mercapto groups, halogen atoms, amino groups, carbonyl groups or guanidino groups and/or interrupted by oxygen atoms, nitrogen atoms or sulfur atoms, and in the case of mercapto compounds of formula I also their dithio compounds, which is characterized in that the microorganism Nocardia spec. DSM 3306 or its enzymes are allowed to act on a D,L-imidazolidinedione derivative of general formula II

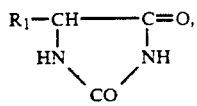

$$R_1-CH\text{------}C=O, \quad (II)$$
$$\phantom{R_1-}HN\quad NH$$
$$\phantom{R_1-CH}CO$$

in which $R_1$ has the above-named meaning or, in the case of mercapto compounds of formula II, also on their dithio compounds.

The D,L-imidazolidinedione derivatives of general formula II and therefore also L-amino acids of general formula I produced from them can carry as substituents $R_1$, for example, the methyl group, the ethyl group, the propyl group, the 1-methylethyl group, the butyl group, the 1-methylpropyl group, the 2-methylpropyl group, the 1,1-dimethylethyl group, the pentyl group, the 1-methylbutyl group, the 3-methylbutyl group or the hexyl group. Especially preferred alkyl groups $R_1$ are those with at most 6 carbon atoms, such as the methyl group of the process product alanine, the 1-methylethyl group of valine, the 2-methylpropyl group of leucine, the 1-methylpropyl group of isoleucine or the ethyl group of the alpha-aminobutyric acid.

The alkyl groups $R_1$ can optionally be substituted by hydroxy groups, mercapto groups, halogen atoms, amino groups, carbonyl groups or guanidino groups, and single substituted alkyl groups are preferred, or can be interrupted by oxygen atoms (preferably one), nitrogen atoms (preferably one or two) or sulfur atoms (preferably one). As alkyl groups, which are substituted by hydroxy groups or mercapto groups, there can be especially emphasized the hydroxymethyl group of serine, the 1-hydroxyethyl group of threonine, the mercaptomethyl group of cysteine, the 2-mercaptoethyl group of homocysteine and the 1-mercapto-1-methylethyl group of beta-thiovaline. As an alkyl group $R_1$ interrupted by a sulfur atom there can be emphasized the 2-methyl thioethyl group of methionine. Alkyl groups $R_1$, which carry an amino group or a guanidino group as substituents $R_1$, are, for example, the 2-amino ethyl group of the alpha,gamma-diaminobutyric acid, 3-aminopropyl group of ornithine, the 3-guanidinopropyl group of arginine and the 4-aminobutyl group of lysine. Suitable as oxy-or oxoalkyl groups $R_1$ are preferably those that also additionally are substituted by a hydroxy group, amino group or guanidino group and/or are interrupted by an oxygen atom or a nitrogen atom—more precisely an imino group; such groups are, for example, the acetoxymethyl group of 0-acetylserine, the 1-acetoxyethyl group of 0-acetylthaeonne, the carboxymethyl group of asparaginic acid, the 2-carboxyethyl group of glutaminic acid, the 2-methoxy-2-oxoethyl group of the omega-asparaginic acid monomethyl ester, the 3-guanidinooxy group of citruline or the 3-guanidino-3-oxopropyl group of canavanine.

The process according to the invention is performed by the use of the microorganism Nocardio spec. DSM 3306. This microorganism was isolated as earth samples, by it being mixed with a mineral salt medium, which contained 5-(2-methylpropyl)-hydantoin as sole nitrogen source, incubated and the grown culture are plated out on agar plates, which also contain 5-(2-methylpropyl)-hydantoin as sole nitrogen source.

The microorganism obtained was deposited at the German Collection of microorganisms (Deutsche Sammlung von Mikroorganismen, Grisebachstr. 8, D-3400 Goettingen) on May 9, 1985, and received the number DSM 3306 there. It is irrevocably available to experts.

Taxonomically, it has the following properties:

| | |
|---|---|
| Colony morphology | round, irregular edge, not translucent |
| Cell morphology | in young cultures bacilli 1.2 micrometers thick, 8-20 micrometers long, they fragment to bacilli of 2-5 micrometers long, branchless, immobile |
| Gram stain | gram-positive |
| Acid resistance | negative |
| Endospores | negative |
| Oxygen ratio | obligate aerobe |
| Catalase | positive |
| Oxidase | positive |
| Temperature optimum | 30-37° C. |
| Citrate utilization | negative |
| Nitrite from nitrate | positive |
| Indole formation | negative |
| Methyl red | negative |
| Voges-Proskauer | negative |
| Urease | negative |
| H2S formation | negative |
| Gelatin liquefaction | positive |
| Starch hydrolysis | positive |
| Sugar utilization | acids from saccharose, glucose, fructose, arabinose no gas formation |
| NaCl tolerance | up to 5% |

On the basis of its morphological and physiological properties the strain, according to "Bergey's Manual of Determinative Bacteriology," 8th edition (1974), was provisionally classified in the genus Nocardia.

Under the culture conditions usually used in a suitable nutrient medium this microorganism is cultured under aeration, under submerged cultures. Then the substrate (preferably dissolved in a suitable solvent) is added to the culture and fermented until a maximum substrate conversion is achieved.

Suitable substrate solvents are, for example, water, methanol, ethanol, glycol monomethyl ether, dimethylformamide or dimethyl sulfoxide.

. The optimal substrate concentration, the substrate addition time and the fermentation duration depend on the structure of the substrate used and the kind of fermentation conditions used. These magnitudes, as is generally necessary in microbiological steroid conversions, must be determined in particular cases by preliminary tests, as are familiar to one skilled in the art. During fermentation the pH of the fermentation broth is preferably set at a pH value of 7.5-10.

On the other hand, it is possible to separate the grown microorganism from the culture medium, for example, by filtering or centrifuging, optionally to immobilize it by one of the known methods and to perform the fermentation of the substrate with the isolated cell mass in the resting cell process or by means of immobilizates.

The following embodiments illustrate the process of the invention.

EXAMPLE 1

A 500-ml Erlenmeyer flask with 100 ml of sterile nutrient medium containing 0.5 g of meat extract, 0.5 g of peptone, 0.5 g of yeast extract and 0.2 g of sodium chloride is inoculated with Nocardia spec. DSM 3306 and shaken for 20 hours at 30° C. with 180 revolution per minute. Then the cell mass is separated by centrifuging and washed with physiological saline solution.

400 mg of moist cell mass is suspended 10 ml of 0.1M tris/HCl buffer of pH 8.5, mixed with 10 mg of 5-(2-methylpropyl)-hydantoin and incubated for 24 hours at 30° C. By determination with L-amino acid oxidase it is determined that 7.9 mg of L-leucine has formed.

EXAMPLE 2

3.5 mg of L-isoleucine is formed from 10 mg of 5-(1-methylpropyl)-hydantoin under the conditions of example 1.

EXAMPLE 3

2.5 mg of L-valine is formed from 10 mg of 5-(1-methylethyl)-hydantoin under the conditions of example 1.

EXAMPLE 4

2.1 mg of cystine is formed from 10 mg of 5,5'-dithiobismethylene-bis-hydantoin under the conditions of example 1.

EXAMPLE 5

A 2-liter Erlenmeyer flask with 500 ml of sterile nutrient medium containing 2.5 g of meat extract, 2.5 g of peptone, 2.5 g of yeast extract and 1 g of sodium chloride is inoculated with 50 ml of a 20-hour-old culture of Nocardia spec. DSM 3306—produced according to example 1—and shaken for 20 hours at 30° C. with 180 revolution per minute. Then the cell mass is separated by centrifuging and washed with physiological saline solution.

8 g of moist cell mass is suspended in 200 ml of 0.1M tris/HCl buffer of pH 8.5, mixed with 1.0 g of 5-(2-methylpropyl)-hydantoin and incubated for 24 hours at 30° C. Then the cell mass is centrifuged off and from the filtrate 660 mg of L-leucine is isolated with a point of decomposition of 291° C. (from aqueous ethanol) $[\alpha]_D^{20} = +15.6°$ (20% aqueous hydrochloric acid).

EXAMPLE 6 a) 3.5 g of moist cell mass of Nocardia spec. DSM 3306—produced according to example 5—is suspended in 31.5 g of 2% aqueous solution of sodium alginate and instilled into 500 ml of a 0.1M aqueous solution of calcium chloride dihydrate.

b) 1.5 g of the immobilizate thus obtained is suspended in 10 ml of 0.1M of tris/HCl buffer of pH 8.5, mixed with 10 mg of 5-(2-methylpropyl)-hydantoin and incubated 18 hours at 30° C. By determination with L-amino acid oxidase it is determined that 7.8 mg of L-leucine has formed.

EXAMPLE 7

3.2 mg of L-isoleucine is formed from 10 mg of 5-(1-methylpropyl)-hydantoin under the conditions of example 6b.

EXAMPLE 8

2.1 mg of L-valine is formed from 10 mg of 5-(1-methylethyl)-hydantoin under the conditions of example 6b.

EXAMPLE 9

4.1 mg of cystine is formed from 10 mg of 5,5'-dithiobismethylene-bis-hydantoin under the conditions of example 6b.

We claim:

1. A process for the production of L-amino acids of formula I

wherein $R_1$ is an alkyl radical having 1 to 12 carbon atoms optionally substituted by hydroxy groups, mercapto groups, halogen atoms, amino groups, oxo groups or guanidino groups and/or interrupted by oxygen atoms, imino groups or sulfur atoms, or, in the case of mercapto compounds of formula I, a dimer thereof, comprising contacting Nocardia spec. DSM 3306 or its enzymes with a D,L-imidazolidinedione derivative of formula II

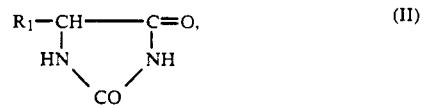

wherein $R_1$ has the above-named meaning or, in the case of mercapto compounds of formula II, with a dimer thereof.

2. A process for the production of L-amino acids of formula Ia

wherein $R_2$ is an alkyl radical having 1 to 6 carbon atoms optionally substituted by a hydroxy group, a mercapto group, a methylthio group, an amino group, a carboxyl group or a guanidino group or, in the case of mercapto compounds of formula Ia, a dimer thereof, comprising contacting Nocardia spec. DSM 3306 or its enzymes with a D,L-imidazolidinedione derivative of formula IIa

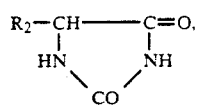

(IIa)

wherein
R$_2$ has the above-named meaning or, in the case of mercapto compounds of formula IIa, with a dimer thereof.

3. A process for the production of L-amino acids of formula Ib

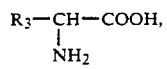

(Ib)

wherein
R$_3$ is an alkyl radical having 1 to 6 carbon atoms, a mercapto methyl group or a grouping of formula III

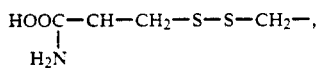

(III)

comprising contacting Nocardia spec. DSM 3306 or its enzymes with a D,L-imidazolidinedione derivative of general formula IIb

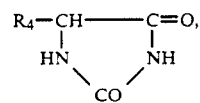

(IIb)

wherein
R$_4$ is an alkyl radical having 1 to 6 carbon atoms, a mercapto methyl group or the grouping of formula IV

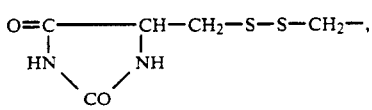

(IV)

wherein R$_3$ and R$_4$ are defined correspondingly.

4. A process of claim 1, wherein the D,L-imidazolidinedione derivative is 5-(2-methylpropyl)-hydantoin.

5. A process of claim 1, wherein the D,L-imidazolidinedione derivative is 5-(1-methylpropyl)-hydantoin.

6. A process of claim 1, wherein the D,L-imidazolidinedione derivative is 5-(1-methylethyl)-hydantoin.

7. A process of claim 1, wherein the D,L-imidazolidinedione derivative is 5,5'-dithiobismethylene-bis-hydantoin.

8. A process of claim 1, wherein the Nocardia is immobilized.

* * * * *